(12) United States Patent
Keller

(10) Patent No.: US 8,192,493 B2
(45) Date of Patent: Jun. 5, 2012

(54) PROSTHESIS FOR BRIDGING A VERTEBRAL BODY

(75) Inventor: Arnold Keller, Kayhude (DE)

(73) Assignee: Cervitech, Inc., San Diego, CA (US)

( * ) Notice: Subject to any disclaimer, the term of this patent is extended or adjusted under 35 U.S.C. 154(b) by 224 days.

(21) Appl. No.: 12/683,919

(22) Filed: Jan. 7, 2010

(65) Prior Publication Data

US 2010/0131066 A1 May 27, 2010

Related U.S. Application Data

(63) Continuation of application No. 11/137,707, filed on May 26, 2005, now abandoned.

(30) Foreign Application Priority Data

Sep. 23, 2004 (EP) .................................. 04022671

(51) Int. Cl.
- *A61F 2/44* (2006.01)
- *A61B 17/70* (2006.01)
- *A61B 17/88* (2006.01)

(52) U.S. Cl. ..................................... 623/17.11; 606/279
(58) Field of Classification Search .... 623/17.11–17.16; 606/246, 279
See application file for complete search history.

(56) References Cited

U.S. PATENT DOCUMENTS

| | | |
|---|---|---|
| 4,636,217 A | 1/1987 | Ogilvie et al. |
| 4,657,550 A | 4/1987 | Daher |
| 4,892,545 A | 1/1990 | Day et al. |
| 4,932,975 A | 6/1990 | Main et al. |
| 5,423,816 A | 6/1995 | Lin |
| 5,522,899 A | 6/1996 | Michelson |
| 5,534,029 A | 7/1996 | Shima |
| 5,658,335 A | 8/1997 | Allen |
| 5,800,547 A | 9/1998 | Schafer et al. |
| 5,800,550 A | 9/1998 | Sertich |
| 5,895,428 A | 4/1999 | Berry |
| 6,113,637 A | 9/2000 | Gill et al. |
| 6,176,882 B1 | 1/2001 | Biedermann et al. |

(Continued)

FOREIGN PATENT DOCUMENTS

DE 4109941 10/1992

(Continued)

OTHER PUBLICATIONS

Keller, U.S. Office Action mailed Mar. 26, 2010, directed to related U.S. Appl. No. 11/125,313; 10 pages.

(Continued)

*Primary Examiner* — Eduardo C Robert
*Assistant Examiner* — David Comstock
(74) *Attorney, Agent, or Firm* — NuVasive, Inc.; Jonathan Spangler; Marjorie Jarvis

(57) ABSTRACT

A prosthesis for the partial replacement of a vertebral body includes an upper contact plate for connection to an upper vertebral body, a lower contact plate for connection to a lower vertebral body and a bridging part which connects the upper and lower contact plates to one another and bridges at least one intermediate vertebral body which is located between the upper and lower vertebral bodies and is to be partially replaced. The bridging part is accommodated in a recess in the vertebral body and is secured in the recess with lateral anchoring projections which penetrate into the bone substance located on both sides of the bridging part. The cross section of the bridging part may narrow toward the rear, preferably in a trapezoid shape.

9 Claims, 1 Drawing Sheet

U.S. PATENT DOCUMENTS

| | | |
|---|---|---|
| 6,179,873 B1 | 1/2001 | Zientek |
| 6,344,057 B1 | 2/2002 | Rabbe et al. |
| 6,375,683 B1 | 4/2002 | Crozet et al. |
| 6,432,107 B1 | 8/2002 | Ferree |
| 6,440,169 B1 | 8/2002 | Elberg et al. |
| 6,447,546 B1 | 9/2002 | Bramlet et al. |
| 6,527,803 B1 | 3/2003 | Crozet et al. |
| 6,723,126 B1 | 4/2004 | Berry |
| 6,767,367 B1 | 7/2004 | Michelson |
| 6,770,096 B2 | 8/2004 | Bolger et al. |
| 6,808,538 B2 | 10/2004 | Paponneau |
| 7,018,417 B2 | 3/2006 | Kuoni et al. |
| 7,318,839 B2 | 1/2008 | Malberg et al. |
| 2002/0128652 A1 | 9/2002 | Ferree |
| 2002/0165613 A1 | 11/2002 | Lin et al. |
| 2004/0088054 A1 | 5/2004 | Berry |
| 2004/0254644 A1 | 12/2004 | Taylor |
| 2005/0004673 A1 | 1/2005 | Kluger |
| 2006/0064167 A1 | 3/2006 | Keller |
| 2006/0064168 A1 | 3/2006 | Keller |

FOREIGN PATENT DOCUMENTS

| | | |
|---|---|---|
| DE | 20115281 | 1/2002 |
| DE | 101 45 668 | 4/2003 |
| EP | 0560140 | 9/1993 |
| EP | 0567424 | 10/1993 |
| EP | 0951879 | 10/1999 |
| EP | 1104665 | 6/2001 |
| EP | 1290993 | 3/2003 |
| EP | 1417940 | 5/2004 |
| FR | 2846876 | 5/2004 |
| WO | WO-01/03614 | 1/2001 |
| WO | WO-2004/080356 | 9/2004 |

OTHER PUBLICATIONS

International Search Report dated Aug. 10, 2005, directed to PCT/EP05/006317; 3 pages.

EP Search Report dated Feb. 17, 2005, issued in related application No. EP04022670; 3 pages.

Keller, U.S. Office Action mailed Feb. 26, 2007, directed to U.S. Appl. No. 11/125,313; 6 pages.

Keller, U.S. Office Action mailed Sep. 20, 2007, directed to U.S. Appl. No. 11/125,313; 7 pages.

Keller, U.S. Office Action mailed May 30, 2008 directed to U.S. Appl. No. 11/125,313; 7 pages.

Keller, U.S. Office Action mailed Dec. 24, 2008, directed to U.S. Appl. No. 11/125,313; 9 pages.

Keller, U.S. Office Action mailed Jul. 7, 2009, directed to U.S. Appl. No. 11/125,313; 9 pages.

Keller, U.S. Office Action mailed Feb. 23, 2007, directed to U.S. Appl. No. 11/137,707; 6 pages.

Keller, U.S. Office Action mailed Sep. 21, 2007, directed to U.S. Appl. No. 11/137,707; 7 pages.

Keller, U.S. Office Action mailed Dec. 26, 2008, directed to U.S. Appl. No. 11/137,707; 7 pages.

Keller, U.S. Office Action mailed Jul. 7, 2009, directed to U.S. Appl. No. 11/137,707; 6 pages.

Fig. 1
Fig. 2
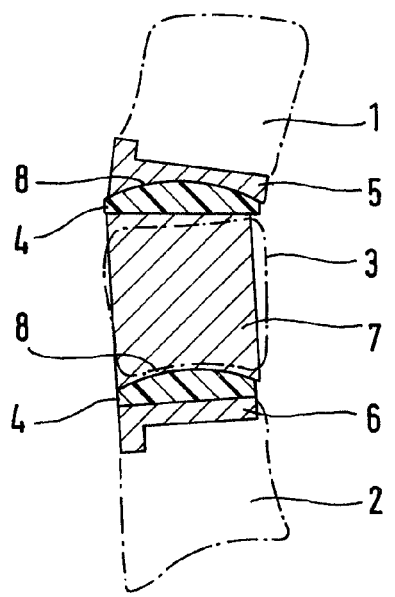
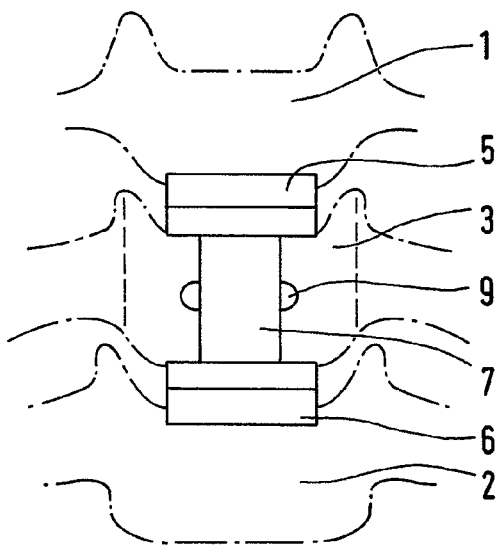
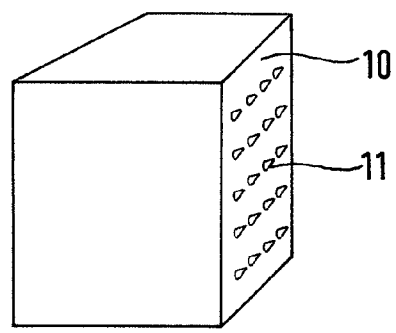
Fig. 3

PROSTHESIS FOR BRIDGING A VERTEBRAL BODY

REFERENCE TO RELATED APPLICATIONS

This application is a continuation of U.S. application Ser. No. 11/137,707, filed May 26,2005, which claims priority from European Application No. 04022671.4, filed Sep. 23, 2004, the entire contents of which are incorporated herein by reference.

FIELD OF THE INVENTION

The invention relates to a prosthesis for partial replacement of a vertebral body that includes an upper contact plate that is configured to connect to an upper vertebral body, a lower contact plate that is configured to connect to a lower vertebral body and a bridging part which connects the upper and lower contact plates to one another.

BACKGROUND OF THE INVENTION

This is based on a known prosthesis (DE-A-4109941, FIG. 2) which comprises an upper contact plate for connection to an upper vertebral body, a lower contact plate for connection to a lower vertebral body, and a bridging part which connects the upper and lower contact plates and is designed for bridging at least one vertebral body which is located between the upper and lower vertebral bodies and whose function is to be replaced by the prosthesis. Between the bridging body and the contact plates, a hinge is in each case provided for replacement of the intervertebral discs. The cross-sectional size of the bridging part is considerably smaller than that of this vertebral body. If the latter is more or less completely preserved, the bridging part should be fitted into it in such a way that it is completely embedded therein. How this could be done surgically is unclear. If it is still more or less complete only on the vertebral arch side, a recess is created on its front face and the bridging part is inserted into said recess. For firm connection to the vertebral body, the bridging part has laterally protruding webs which contain an oblong hole for receiving a securing screw. The securing of the prosthesis on the vertebral body determines, in addition to the facet articulations, the position of said vertebral body with respect to the adjacent vertebral bodies. Only when those surfaces of the adjacent vertebral body intended for the securing webs to bear on are worked in such a way that the vertebral body, after connection to the webs, can maintain its natural position defined by the facet articulations, is there any prospect of the prosthesis fitting in a way that does not cause discomfort. Such precise working is difficult to achieve. It has also been found that securing by means of a screw is not reliable enough.

In another known spinal column prosthesis (U.S. Pat. No. 5,423,816), the bridging part is formed by a coil spring which, because of its compliance, has the purpose of permitting a relative movement of the upper and lower vertebral bodies with respect to one another and to the bridged vertebral body. The coil spring is intended to be received in a cavity inside the vertebral body to be bridged, which is also filled with bone chips which may possibly permit new growth of bone tissue inside the cavity. However, because of their constant relative movement, a firm connection between the turns of the coil spring and the bone tissue is not possible. Therefore, the turns of the coil spring do not form a securing means with respect to the bridged vertebral body. On the contrary, the turns of the coil spring which are being constantly moved relative to the bridged vertebral body are a cause of persistent irritation.

A spinal column prosthesis is also known (EP-A-1417940) in which the bridging part has a U-shaped configuration in side view, so as to engage with its branches on the lower face and upper face of the vertebral body to be replaced. The web lies on the front face of the vertebral body and is screwed onto it. This requires suitable working of the vertebral body on its upper, lower and front faces, which can be difficult, especially if the vertebral body is damaged. Spinal column prostheses are also known in which the bridging part completely replaces the vertebral body (EP-A-567424, WO 0103614, DE-U-20115281, U.S. Pat. No. 5,895,428). This has the disadvantage that a supporting connection is not really possible between the remaining parts of the vertebra and the bridging part.

In another known group of spinal column prostheses (U.S. Pat. No. 4,892,545, U.S. Pat. No. 4,636,217), the bridging part is connected rigidly to the upper and lower vertebral bodies, so that these too are rigidly connected to one another. The bridged vertebral body is in this way kept free from forces and therefore does not require any supporting connection to the bridging part of the prosthesis.

SUMMARY OF THE INVENTION

The object of the invention is therefore to make available a spinal column prosthesis of the type mentioned at the outset which can also be used when the vertebral body to be replaced is completely or to a large extent preserved. A further aim is that a comparatively simple operating technique will permit a good supporting connection between the implant and the vertebral body to be replaced.

This is achieved by the features of the invention as broadly disclosed herein. It is comparatively easy to create a recess in the vertebral body starting from the front face, which recess matches the shape of the bridging part and receives the latter substantially in its entirety. The bridging part is accordingly designed narrower than the vertebral body. By virtue of the mutual positive engagement between the bridging part and the recess, the bridging part and the vertebral body support each other. The bridging part is also unable to escape from the recess, because its lateral projections hold it securely in the recess.

A dowel for rigid connection of adjacent vertebral bodies is known (US-A-2002/0128652) which has a rectangular cross section and is fitted into a correspondingly shaped ventral recess in the vertebral body in question and is equipped with means intended to prevent its escaping from the recess. However, it is not possible to tell how these means are designed. The mutual supporting action and the securing afforded by the lateral projections of the bridging part are all the more effective, the more precisely the recess is adapted to the shape of the bridging part. This is achieved most easily if the cross-sectional shape of the recess is rectangular or trapezoid. This also has the advantage that the side surfaces of the bridging part are large and thus make it easier to accommodate a plurality of anchoring projections. This is especially the case when these are arranged rigidly on the bridging part, for example in the form of a large number of small points. These are expediently designed so that, when the bridging part is pressed into the recess, they find their way to their anchoring position through the elastic or plastic compliance of the bone tissue. In this connection, the bridging part shape narrowing in cross section in the dorsal direction has the further advantage that, as the bridging part is wedged into the vertebral body recess likewise narrowing in cross section in the dorsal direction, the projections are sunk into the bone substance. They can also have a self-cutting design. Another possible embodiment is one in which the projections are made very small in the form of a surface roughness. This is generally sufficient to create an initial strength of the implant/bone connection and, after a short time, to permit permanent connection by means of bone tissue growing into the surface roughness. The projections can be barb-shaped in order to provide minimal resistance to the movement of the implant into the recess of the bone, but to provide greater resistance to its removal from the recess.

At least on the side surfaces, the bridging part can have openings or pores for receiving bone tissue. These can be filled with bone chips before implantation. Over the course of time, living bone tissue grows in, so as to permit firm union between the implant and the bones.

The invention has particular advantages when applied to the cervical spine.

BRIEF DESCRIPTION OF THE DRAWINGS

The invention is explained in more detail below with reference to the drawing which depicts advantageous illustrative embodiments. In the drawing:

FIG. 1 shows a longitudinal section through an illustrative embodiment in the median plane, FIG. 2 shows a front view of the same implant, and FIG. 3 shows a perspective view of the bridging part.

DETAILED DESCRIPTION OF THE INVENTION

FIG. 2 shows an upper vertebral body 1 and a lower vertebral body 2 and, between them, the vertebral body 3 which is to be replaced. A spinal column prosthesis is inserted between the upper and lower vertebral bodies. This prosthesis comprises an upper contact plate 5 connected to the upper vertebral body 1, a lower contact plate 6 connected to the lower vertebral body 2, and a bridging part 7 which connects the plates 5 and 6. Located between the contact plates 5 and 6 and the bridging part 7 there is in each case a hinge (for example according to EP-A-560140) with a hinge surface 8. This is formed, in the upper hinge, on the one hand by the bottom face of the contact plate 5 and on the other hand by a hinge part 4 connected to the bridging part 7 in a manner not shown. In the lower hinge, it is formed on the one hand by the bottom face of the bridging part 7 and on the other hand by the hinge part 4, which is connected to the lower contact plate 6 in a manner not shown. Instead of a hinge with a spherical hinge surface, another hinge type can also be used, for example one with a flexible cushion (DE-U-20115281) or with a spiral spring (DE-A-4109941). If the upper vertebral body 1 and the lower vertebral body 2 are to be rigidly connected, the hinges can also be omitted altogether. Finally, it is possible to use just one hinge between the upper contact plate 5 and the bridging part 7, or between the lower contact plate 6 and the bridging part 7.

While the contact plates 5 and 6 have a customary size which is dimensioned in the interest of low pressure forces between the contact plates and the associated vertebral bodies, the bridging part 7 has a width which is smaller than that of the associated vertebral body 3, that is to say small enough to ensure that the bridging part can be inserted into a recess which has been worked into the relevant vertebral body 3 from the front face and the bone substance remaining alongside it suffices for securely anchoring the bridging part in the recess.

At least part of the recess has a shape which corresponds as exactly as possible to the shape of the bridging part 7. It is thus possible for the surface of the implant to bear on the artificially created surface of the bone in a manner substantially free from play. On the one hand, this provides a good mutual support. On the other hand, it affords the possibility of bone growth creating a stable connection between the bone and the implant. Finally, this ensures that the anchoring projections 9 provided on the implant engage in the bone tissue along substantially their full length in order to be able to transmit the anchoring forces.

The object of providing shape correspondence between the bridging part and the recess created in the bone is achieved most easily with a trapezoid shape of the cross section of the bridging part, as is indicated in FIG. 3. It is also possible to use other cross-sectional shapes, but preferably ones which narrow from the front toward the rear so that, when the bridging part is inserted into the recess, the side surfaces bear on the resected bone surfaces in said manner free from play.

The feature according to which the bridging part has a rearwardly narrowing, in particular trapezoid, shape ought to merit protection independently of the invention as broadly disclosed herein.

The anchoring projections are arranged rigidly on the side surfaces 10 of the bridging part 7. According to FIG. 3, they are in the form of a large number of small, pointed elevations 11 which force themselves into the bone surface as the implant is inserted into the recess in the vertebra. In an alternative embodiment not shown, they are larger and in the form of blades, the plane of the blades extending in the direction of insertion so that they cut into the bone substance. Another embodiment uses micro-projections in the form of a surface roughness that covers the entire side surface 10 or a substantial part thereof. In each case, in addition to the anchoring projections, it is possible to provide openings 12 or pores into which bone substance can grow and anchor itself. To accelerate this process, the openings can be filled from the start with bone chips. It is also possible to coat the implant with osteoconductive or osteoinductive substance.

The invention claimed is:

1. A method for partial replacement of a vertebral body comprising:

establishing an operative corridor through a patient's skin to a target vertebral body;

performing a partial corpectomy of the target vertebral body by forming a recess in the target vertebral body having a cross-sectional shape that in transverse section is narrower than a width of the target vertebral body and that in sagittal section narrows from the front toward the rear direction; and implanting a prosthesis, the prosthesis having an upper contact plate adjacent a superior vertebral body, a lower contact plate adjacent an inferior vertebral body, a bridging part having a trapezoidal cross-section and lateral surfaces configured with rigid anchoring projections, and at least one hinge configured to connect the bridging part to the upper contact plate or lower contact plate, within the recess of the target vertebral body such that the rigid anchoring projections are anchored into the recess as the bridging part is implanted in the target vertebral body.

2. The method of claim 1, wherein the bridging part has openings or pores formed therein for receiving bone tissue.

3. The method of claim 2, further comprising filling the bridging part with bone material or bone replacement material.

4. The method of claim 1, further comprising coating the bridging part with an osteoconductive substance or osteoinductive substance.

5. The method of claim 1, wherein the anchoring projections comprise a plurality of pointed elevations.

6. The method of claim 1, wherein the rigid anchoring projections comprise a barb shape.

7. The method of claim 1, wherein the rigid anchoring projections comprise a self-cutting design.

8. The method of claim 1, wherein the rigid anchoring projections comprise blades.

9. The method of claim 8, wherein a plane of the blades extends in the direction of insertion.

* * * * *